United States Patent [19]

Gardineer et al.

[11] 4,401,882
[45] Aug. 30, 1983

[54] PLUMBING FITTING

[75] Inventors: Bayard G. Gardineer, Skillman; James A. Heringes, Dayton, both of N.J.

[73] Assignee: Technicare Corporation, Solon, Ohio

[21] Appl. No.: 296,091

[22] Filed: Aug. 26, 1981

[51] Int. Cl.³ .......................... F24H 9/12; H05B 3/06
[52] U.S. Cl. .................................. 219/335; 219/381; 219/299; 219/307; 285/156
[58] Field of Search ............... 219/335, 336, 381, 341, 219/296, 297, 299, 306, 307, 308, 309; 237/68; 285/392, 357, 156; 122/13 A, 4 A

[56] References Cited

U.S. PATENT DOCUMENTS

| | | | |
|---|---|---|---|
| 1,281,157 | 10/1929 | Hadaway | 219/306 |
| 1,796,061 | 3/1931 | Swanson | 285/357 |
| 2,250,623 | 7/1941 | Breen | 219/296 |
| 4,282,880 | 8/1981 | Gardineer | 128/660 |

FOREIGN PATENT DOCUMENTS 579942 of 0000 Canada ............................... 219/306

*Primary Examiner*—B. A. Reynolds
*Assistant Examiner*—Teresa J. Walberg
*Attorney, Agent, or Firm*—Donal B. Tobin

[57] ABSTRACT

An annular fitting for connecting an immersion heater into a circulating fluid system which includes a groove cut across the threads on the inside of the fitting and a hole through the fitting wall in fluid communication with the groove. The groove and the hole permit a small quantity of fluid to bleed past the base of the heater to reduce the build up of bubbles around the base of the heater.

2 Claims, 4 Drawing Figures

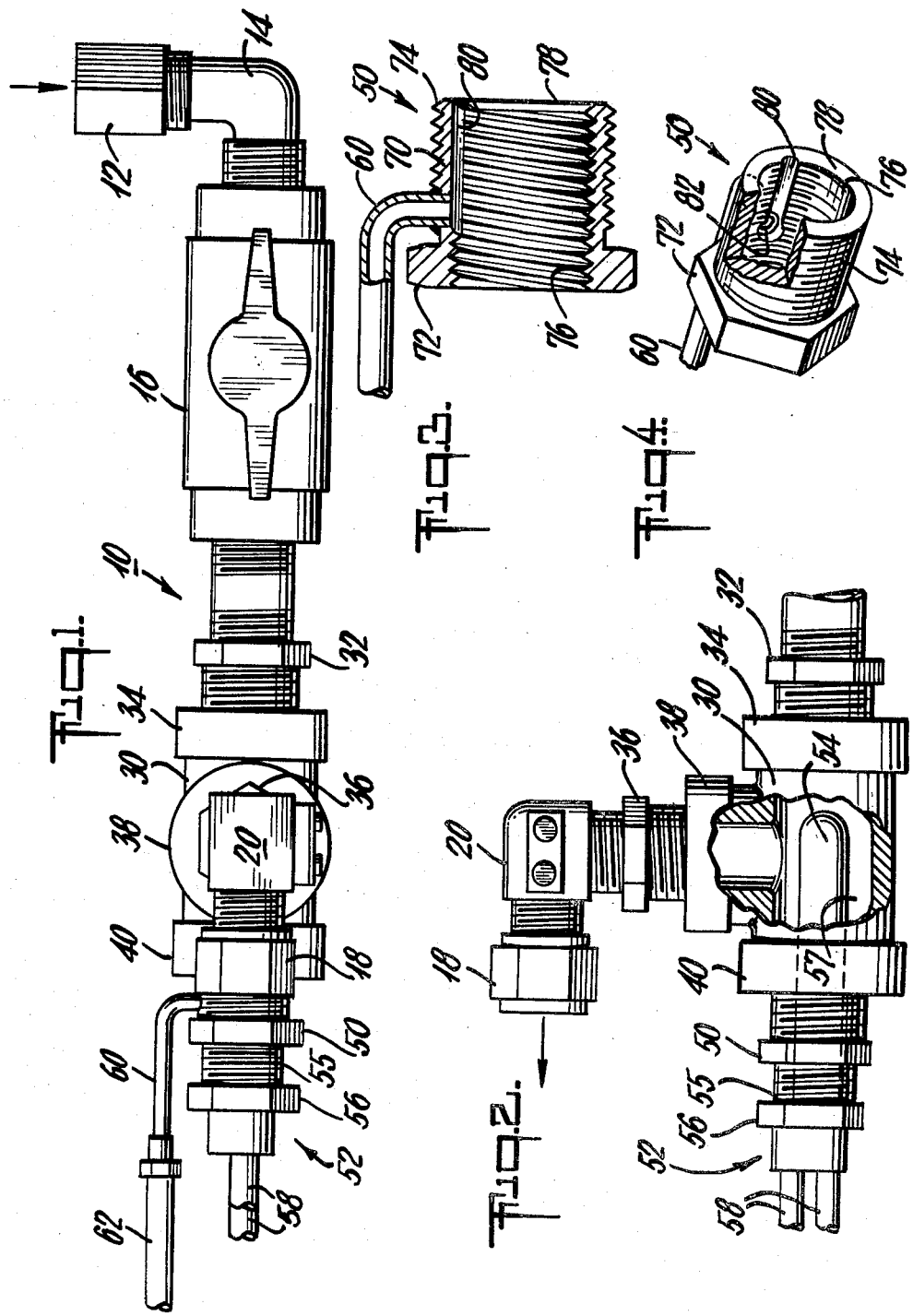

PLUMBING FITTING

FIELD OF THE INVENTION

The present invention relaes to a fitting for a plumbing system and, more particularly, to a fitting for an immersion heater.

BACKGROUND OF THE INVENTION

It is often desirable to maintain the temperature of a reservoir of fluid, for example water, within a predetermined temperature range. Placing an immersion heater directly in the reservoir will, of course, heat the water, but it is likely to introduce thermal gradients and convection currents which will cause the temperature in the reservoir to vary from one point to another. Thus, where it is important to maintain the temperature of the entire reservoir uniform without thermal current, a closed circulating system can be used into which an immersion heater may be placed at a point removed from the reservoir.

One particular system that requires a reservoir of uniform temperature is an ultrasound mammary scanning apparatus of the kind disclosed in U.S. Pat. No. 4,282,880, issued Aug. 11, 1981. The inventors listed on U.S. Pat. No. 4,282,880 are the same as the inventors of the present invention, and that patent is assigned to the assignee of the present patent application. The specification of U.S. Pat. No. 4,282,880 is incorporated herein by reference.

In the system described in this patent, a scanning transducer and associated sonic less are submerged in water. Subjects are positioned on an examination table with the breast projecting through an aperture in the table into the tank of water in which the ultrasound equipment is enclosed. It is necessary to condition the water used for the ultrasound transmission medium to remove sources of interference that could distort the ultrasound image. Water conditioning may involve filtering of particulate matter, removing bubbles, inhibiting bacteria growth and maintaining uniform temperature to eliminate thermal gradients, all of which can interfere with ultrasound transmission. In the water circulation and maintenance system disclosed in this U.S. Pat. No. 4,282,880, the water transmission medium is divided into two separate pools by means of a flexible bag. The first pool consists of the water collected in the main tank in which the ultrasound transducing equipment is placed. The patient's breast is suspended in a separate but smaller pool of water separated from the water in the main tank by a flexible bag. Thus, the portion of the water in contact with the patient may be changed regularly for aesthetic and sanitary reasons without having to change the water in the entire system.

When the water in the bag is changed, it is necessary to filter particulate matter, remove bacteria and equalize the temperature of the newly added water to that of the water which remains in the main tank.

The temperature of the water in both pools is maintained uniform by circulating in water through two separate but interdependent circulating systems, both of which include an immersion heater. The immersion heater may be spliced into the fluid circulation line using a conventional T-joint, with one arm of the T-joint providing an inlet, a second arm of the T-joint providing an outlet and the third arm of the T-joint supporting the heater itself. The space provided inside the T-joint acts as a reservoir to permit water to circulate completely about the heating element.

In systems such as that described in U.S. Pat. No. 4,282,880, the amount of water maintained in the system and the circulation flow rates are both low, so that it is not practical to use large immersion heaters. What is required is a relatively small immersion heater.

We have found that when such heaters are spliced into a circulating system of this kind, air bubbles can be generated around the base of the heater and can be trapped so that a large air bubble can build up which permits the heater to overheat and sometimes burn out. It is confined system such as this, where it is not feasible to provide large, separate reservoirs for the heating element, it is necessary to find a method for preventing this bubble build-up around the base of the heater.

SUMMARY OF THE INVENTION

The present invention solves the problem of bubble build-up around the base of an immersion heater by providing a special kind of fitting for connecting the heater into the system. This fitting which includes a bleeder passage to permit small quantities of fluid to flow continuously by the base of the heating element and out through the fitting. This small quantity of fluid can be returned to the system or discharged. The fitting of the present invention includes a generally annular stem with a cap at one end about which a plumbing tool may be attached to connect the fitting into the system. The outside surface of the stem includes means for connecting the fitting into the plumbing system. The inside surface of the stem includes means for providing a sealed connection with the heater. A fluid passage is included along and/or through the stem portion of the fitting to permit a small quantity of fluid to continuously bleed past the base of the heating element. A conduit may be connected to this fluid passage to carry away the bled fluid either to a discharge reservoir or back into the system at some point removed from the heater.

In the preferred embodiment, the inside surface of the stem and the confronting surface of the heater include cooperating threads. In this preferred embodiment, the fluid passage includes a groove running axially along the inside surface of the stem at the root of these threads. The groove extends from the free end of the fitting to a point less than the full distance of the cooperating surface of the threads on the inside surface of the stem and the heater. A hole is placed through the stem wall in fluid communication with the groove. The conduit is sealed around this hole in fluid communication with the passage through the hole.

Instead of a groove along the threads of the inside surface of the stem portion of the fitting, a groove may be placed on the cooperating threads of the heater element. The hole in the stem wall would still be used to establish fluid communication with the groove. In a still further alternative, especially with a thick walled stem, the groove could be replaced by an axial hole drilled in the stem wall which would connect to the hole through the stem wall to provide the necessary fluid passage.

Thus, it can be seen that the special fitting of the present invention may be used to connect an immersion heater into a circulating fluid system. If a T-joint is used, this fitting will be inserted sufficiently far into one arm of the T-joint so that the hole through the stem will be completely outside the T-joint and so that the bleeder conduit may be connected about the hole without interfering with the adjacent outside surfaces of the T-joint.

The other two arms of the T-joint can be spliced into the fluid system. The space provided within the T-joint serves as a small reservoir to permit the fluid to circulate completely about the heating element. Any bubbles which may develop at the base of the heater, where it is connected into the T-joint, will be carried away by the small volume of fluid that is permitted to bleed through the groove in the fitting out through the conduit. Thus, the present invention provides a beneficial apparatus for eliminating a major cause of immersion heater burn-out.

These and other features and advantages of the present invention will become apparent from the following detailed description of the preferred embodiments taken in conjunction with the following drawings.

BRIEF DESCRIPTION OF THE DRAWINGS

FIG. 1 shows a plan view of a portion of a fluid system into which an immersion heater is connected using the fitting of the present invention;

FIG. 2 shows a side elevation, partly in section, of the portion of a fluid system shown in FIG. 1;

FIG. 3 shows a cross-sectional view of the fitting of the present invention; and, FIG. 4 shows a perspective view of the fitting shown in FIG. 3.

DETAILED DESCRIPTION OF THE PREFERRED EMBODIMENT

Referring not to FIG. 1, there is shown a portion of a fluid circulating system generally designated as 10, including an input fitting 12 connected to elbow 14, which is in turn connected to shut-off valve 16. Output fitting 18 is connected to elbow 20. A T-joint 30 is spliced into the system between elbow 20 and valve 16 by means of a first fitting 32 connected to a first arm 34 of T-joint 30 and a second fitting 36 connected to a second arm 38 of T-joint 30.

The third arm 40 of T-joint 30 receives the special fitting 50 of the present invention. Heater 52, having a heating element 54 and a connection fitting 56, is received by fitting 50 so that heating element 54 projects into the space 57 defined by the interior surfaces of T-joint 30. Heater 52 is connected to an electrical power source by conventional electric wires 58, which are partially shown in FIG. 2.

Referring now to FIG. 1, there is shown a conduit 60 emanating from special fitting 50. Conduit 60 is connected to tubing 62 which may be connected to a discharge reservoir (not shown) or which may be connected back into the fluid system at some point not shown in the drawing.

Valve 16 may be closed to shut off the water flow so that heater 52 may be replaced without allowing fluid in the remainder of the system to drain.

In FIG. 2, heating element 54 is shown projecting into the space 57 defined by the internal surfaces of T-joint 30. As water or other circulating fluid circulates from valve 16 through T-joint 30 out through output fitting 18, the water will come into intimate contact with heater 54 and be heated. The space 57 provided within T-joint 30 is usually larger than the average inside diameter of the piping used in the rest of the system so that the water in the system may circulate reasonably freely around heating element 54. However, we have found that the water in third arm 40 of T-joint 30 can become reasonably stagnant and can be heated to an excessive degree so that bubbles will begin to develop in the space provided within third arm 40 of T-joint 30. These bubbles create hot spots on the heating element and, if the bubbles are allowed to remain in third arm 40 close to the base of heater element 54, heater element 54 can overheat and even burn out. Thus, it is necessary to provide a means for removing bubbles that may develop in third arm 40 of T-joint 30 away from heater element 54. Special fitting 50 is designed for just that purpose.

Referring now to FIG. 3, there is shown a cross-sectional view of special fitting 50. In FIG. 3, it can be seen that special fitting 50 is a generally annular fitting having a stem portion 70 and a cap portion 72. The outside surface of stem portion 70 includes threads 74 for connecting fitting 50 into third arm 40 of T-joint 30 by cooperating threads on the inside surface of third arm 40. The inside surface of stem portion 70 also includes threads 76 for receiving cooperating threads 55 on the exterior surface of connection fitting 56 of heater 52. Thus, heater 52 is assembled into T-joint 30 by threading heater connection fitting 56 into cooperating threads 76 on the inside surface of stem portion 70 of special fitting 50 and then by threading threads 74 on the outside surface of stem portion 70 of special fitting 50 into cooperating threads on the internal surface of third arm 40 of T-joint 30. Threads 74 and 55 may be replaced by other suitable connection means including brazing.

Still referring to FIG. 3, it can be seen that threads 76 on the inside surface of stem portion 70 of special fitting 50 may extend completely along the inside surface of fitting 50 or the beginning of threads 76 may be spaced somewhat apart from the free end 78 of stem portion 70.

In order to permit bubbles to be bled from the space in the vicinity of third arm 40, a fluid passage 80 is cut across threads 76 on the inside surface of stem portion 70. Fluid passage 80 is shown best in FIG. 4.

Groove 80 extends from free end 78 of stem portion 70 to a point part way along the axial distance of stem portion 70. Opening 82 is placed through the wall of stem portion 72 in fluid communication with passage 80. Fitting 60 is affixed in or about opening 82 by means of welding, threading or brazing or some other suitable water-tight means so that it is in fluid communication with passage 80.

As seen best in FIG. 1, opening 82 in the wall of stem portion 70 should be spaced apart a sufficient distance from free end 78 of of stem portion 70 so that when fitting 50 is inserted in third arm 40 of T-joint 30, opening 82 and the conduit 60, which is attached to it, will not hit against the outside surface of third arm 40 or recede within the opening defined by third arm 40.

Groove 80 is shown in FIG. 4 as extending axially along stem portion 70 and cutting directly across the root of the threads 76.

Threads 76 on the inside surface of stem 70 need not extend all the way to free end 78. Instead thread 76 may be recessed a small distance inside the free end 78 so as to provide an unthreaded, land portion 84 which forms an abutment edge 86. Edge 86 provides a stop for connection fitting 56 on heater 52.

Thus, it can be seen that the special fitting 50 of the present invention provides a method of bleeding bubbles or air that may be trapped in the space within the third arm 40 of T-joint 30 so as to minimize the possibility of air build-up around heater element 54 and to correspondingly minimize the prospects of heater element 54 failing The present invention has been described in conjunction with the preferred embodiment. Those skilled in the art will appreciate that many modifications and changes may be made in the preferred embodiment without departing from the present invention. It is, therefore, not intended to limit the present invention except as set forth in the attached claims.

We claim:

1. A fitting for connecting an immersion heater into a fluid system comprising:
   - a generally annular stem portion having a free end and having a second end;
   - a cap portion affixed to said second end and adapted to be engaged by a plumbing tool;
   - threads on the inside of said stem portion for connecting said fitting to said heater element by means of cooperating threads on said heater element;
   - threads on the outside of said stem portion for connecting said fitting into said fluid system;
   - an axial groove extending transverse to the threads on the inside surface of said stem portion, said groove extending from said free end of said fitting a predetermined distance along said threads;
   - said stem having an opening through its wall in fluid communication with said groove;
   - said groove and said opening permitting a flow of a small quantity of fluid through said fitting to facilitate the removal of undesired bubbles that may be present around the base of said heating element.

2. An apparatus comprising:
   - an immersion heater having a heating element for immersion in a fluid system;
   - a fitting for sealably connecting said heater into said fluid system, said fitting including:
   - a generally annular stem portion having a first free end and having a second end;
   - a cap portion affixed to said second end and adapted to be engaged by a plumbing tool;
   - an axial groove extending from said free end partway along the inside annular surface of said stem; and
   - said stem having an opening therethrough and fluid communication with said groove.

* * * * *